US011160761B2

(12) United States Patent
Brahms et al.

(10) Patent No.: US 11,160,761 B2
(45) Date of Patent: Nov. 2, 2021

(54) SILICA MICROCAPSULES AND METHODS OF PREPARING SAME

(71) Applicant: International Flavors & Fragrances Inc., New York, NY (US)

(72) Inventors: John Brahms, Morris Plains, NJ (US); Ronald Gabbard, Farmingdale, NJ (US); Feng Geng, Fort Worth, TX (US); Julie Ann Wieland, Edison, NJ (US); Li Xu, Edison, NJ (US); Lewis Michael Popplewell, Morganville, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 511 days.

(21) Appl. No.: 16/086,198

(22) PCT Filed: Mar. 20, 2017

(86) PCT No.: PCT/US2017/023155
§ 371 (c)(1),
(2) Date: Sep. 18, 2018

(87) PCT Pub. No.: WO2017/161364
PCT Pub. Date: Sep. 21, 2017

(65) Prior Publication Data
US 2020/0306197 A1 Oct. 1, 2020

Related U.S. Application Data

(60) Provisional application No. 62/310,381, filed on Mar. 18, 2016, provisional application No. 62/397,651, filed on Sep. 21, 2016.

(51) Int. Cl.
| *A61K 9/48* | (2006.01) |
| *A23L 27/00* | (2016.01) |
| *A23P 10/35* | (2016.01) |
| *A21D 2/02* | (2006.01) |
| *A21D 2/16* | (2006.01) |
| *A23G 4/06* | (2006.01) |
| *A61K 8/11* | (2006.01) |
| *B01J 13/08* | (2006.01) |
| *B01J 13/20* | (2006.01) |

(52) U.S. Cl.
CPC ............. *A61K 9/4825* (2013.01); *A21D 2/02* (2013.01); *A21D 2/165* (2013.01); *A23G 4/064* (2013.01); *A23L 27/72* (2016.08); *A23L 27/74* (2016.08); *A23P 10/35* (2016.08); *A61K 8/11* (2013.01); *A61K 9/4816* (2013.01); *B01J 13/08* (2013.01); *B01J 13/206* (2013.01); *A23V 2002/00* (2013.01)

(58) Field of Classification Search
CPC ...... A61K 9/4825; A61K 8/11; A61K 9/4816; A23L 27/00; A23L 27/72; A23L 27/74; A23P 10/30; A23P 10/35; A21D 2/02; A21D 2/165; A23G 4/064; B01J 13/10; B01J 13/14; B01J 13/22; B01J 13/08; B01J 13/206; A23V 2002/00; A61L 9/012; A61L 9/048; A61L 9/01; C08L 1/286; C08L 5/08; C08L 89/06; C08L 5/00; C08L 83/04
See application file for complete search history.

(56) References Cited

U.S. PATENT DOCUMENTS

| 8,449,918 | B2 * | 5/2013 | Lapidot ................ A61K 8/25 424/489 |
| 9,044,732 | B2 | 6/2015 | Lei |
| 9,532,933 | B2 * | 1/2017 | Lei ......................... A61K 8/585 |
| 2004/0256748 | A1 | 12/2004 | Seok |
| 2006/0057090 | A1 | 3/2006 | Buchwald-Werner |
| 2012/0104639 | A1 | 5/2012 | Xu |
| 2012/0237578 | A1 | 9/2012 | Lei |
| 2014/0106032 | A1 * | 4/2014 | Dardelle ............. A61K 9/5036 426/89 |
| 2014/0227329 | A1 | 8/2014 | Habar |
| 2015/0174033 | A1 | 6/2015 | Herrmann |
| 2015/0250689 | A1 | 9/2015 | Dardelle |

FOREIGN PATENT DOCUMENTS

| CN | 102641703 B | 12/2014 |
| JP | 361254243 A | 11/1986 |
| WO | 2009090747 A1 | 7/2009 |

(Continued)

OTHER PUBLICATIONS

Erni, P., et al. (2013) "Turning Coacervates into Biohybrid Glass: Core/Shell Capsules Formed by Silica Precipitation in Protein/Polysaccharide Scaffolds," Angew Chem. Int. Ed. 52:10334-10338.

(Continued)

*Primary Examiner* — Gollamudi S Kishore

(57) ABSTRACT

Disclosed is a microcapsule containing: (i) a microcapsule core having an active material, and (ii) a microcapsule wall formed of a first polymer and second polymer. The first polymer is a sol-gel polymer. The second polymer is gum arabic, purity gum ultra, gelatin, chitosan, xanthan gum, plant gum, carboxymethyl cellulose, sodium carboxymethyl guar gum, or a combination thereof. The weight ratio between the first and second polymer is 1:10 to 10:1. Also disclosed are processes for preparing the microcapsule and uses of the microcapsules in consumer products.

4 Claims, No Drawings

(56) References Cited

FOREIGN PATENT DOCUMENTS

WO     2013174921 A1    11/2013

OTHER PUBLICATIONS

Extended European Search Report dated Oct. 9, 2019 for EP 17767696.2, filed Mar. 20, 2017.
International Preliminary Report on Patentability in PCT/US2017/161364 dated Sep. 18, 2018.
International Search Report and Written Opinion in PCT/US2017/161364 dated Jun. 7, 2017.
Kawashima, Y., et al. (1983) "Polymorphism and drug release behavior of spray-dried microcapsules of sulfamethoxazole with polysaccharide gum and colloidal silica," Drug Development and Industrial Pharmacy 9 (8):1445-1463.

* cited by examiner

SILICA MICROCAPSULES AND METHODS OF PREPARING SAME

CROSS REFERENCE TO RELATED APPLICATIONS

This application is a national stage entry under 35 USC 371 for International Application No. PCT/US2017/023155 filed Mar. 20, 2017, which claims priority to US Patent Application Ser. Nos. 62/310,381 filed Mar. 18, 2016 and 62/397,651 filed Sep. 21, 2016. The contents of the above-mentioned applications are incorporated herein by reference in their entirety.

BACKGROUND

Microcapsules are used in controlled release of flavor, aroma, and nutrient. They also protect sensitive food ingredients from decomposing. Despite of the advances in the microcapsule technology, developing a food-grade microcapsule remains a challenge due to limited materials that are suitable for food consumption.

Sol-gel microcapsules such as silica microcapsules have been used to deliver fragrances for use in personal care products such as antiperspirant products. See U.S. Pat. No. 9,044,732 and US Patent Application Publication Nos. 2012/0104639 and 2004/0256748. These microcapsules contain silica microcapsule wall prepared typically in the presence of cetyltrimethylammonium chloride (CTAC).

Silica, a naturally abundant material, has been recognized as a safe food additive by the Food and Drug Administration and other health organization such as the World Health Organization and the European Food Safety Authority. However, CTAC is a non-food grade emulsifier. The known silica microcapsules prepared from CTAC and other non-food grade dispersants are not suitable to deliver flavor in food products.

Biopolymers such as proteins and polysaccharides are also used to prepare microcapsules. See US 2015/0250689. Erni et al. describes a process of preparing protein hydrogel microcapsules. See Erni et al., *Angew. Chem. Int. Ed.* 52, 10334-38 (2013). A hydrogel microcapsule was first formed with a protein scaffold. Amorphous silica was then deposited on the scaffold, yielding dense shells with low permeability for organic compounds. This process requires the separation of hydrogel microcapsules from the aqueous phase and then their immersion in a pure liquid silica precursor. See id, page 10335. Challenges remain in large scale manufacturing following this process such as prolonged time consumed in separation and use of large amount of costly pure silica precursors.

There is a need to develop a microcapsule that is safe for food consumption to efficiently deliver flavor, aroma, nutrient, etc., and that can be manufactured in a cost effective manner.

SUMMARY

This invention is based on the discovery of certain stable sol-gel microcapsules suitable for use in food.

Accordingly, one aspect of this invention relates to microcapsules each containing (i) a microcapsule core containing an active material, (ii) a microcapsule wall formed of a first polymer and second polymer, and (iii) optionally a food-grade dispersant. The weight ratio between the first and second polymer is 1:10 to 10:1.

The first polymer can be a sol-gel polymer, e.g., a silicon polymer including silica, polydialkylsiloxane such as polydimethylsiloxane and polydiethylsiloxane, etc.

Exemplary second polymers include, but are not limited to, gum arabic, purity gum ultra, gelatin, chitosan, xanthan gum, plant gum, carboxymethyl cellulose, sodium carboxymethyl guar gum, and combinations thereof. In some embodiments, the second polymer is a combination of gum arabic and gelatin present in a weight ratio of 1:5 to 5:1 (e.g., 1:2 to 2:1).

The food-grade dispersant can be selected from the group consisting of quillaja saponin, N-lauroyl-L-arginine ethyl ester, sorbitan esters, lecithins, lyso-lecithins, polyethoxylated sorbitan esters, polyglyceryl esters, fatty acid esters, gum arabic, pectin, carrageenan, chitosan, chondroitin sulfate, cellulose gum, modified starch, whey protein, pea protein, egg white protein, silk protein, gelatin of fish, proteins of porcine or bovine origin, ester gum, fatty acids, and combinations thereof. Typically, the food-grade dispersant is present at a level of 0.3 to 10%, preferably 0.5 to 5%, and more preferably 1 to 3% by weight of the microcapsule.

In some embodiments, the active material is a fragrance, pro-fragrance, flavor, malodor counteractive agent, anti-inflammatory agent, anesthetic, analgesic, anti-viral agent, anti-infectious agent, anti-acne agent, skin lightening agent, insect repellant, emollient, skin moisturizing agent, vitamin or derivative thereof, nanometer to micron size inorganic solid, polymeric or elastomeric particle, taste modulator, probiotic, cell, or combination thereof.

The microcapsule preferably has a particle size in diameter of 1 to 1000 µm (e.g., 5 to 500 µm, 1 to 250 µm, and 10 to 200 µm). In some embodiments, the weight ratio of the microcapsule core:the microcapsule wall can be 50:1 to 1:2, preferably 20:1 to 1:2, and more preferably 10:1 to 1:1. The microcapsule core typically contains 50-100 wt % of the active material. The microcapsule wall in general includes 10-90 wt % of the first polymer and 10-90 wt % of the second polymer.

In some embodiments, the microcapsule has a single-layered microcapsule wall formed of a polymeric network of silica interlocked with a coacervate of gum arabic and gelatin.

In other embodiments, the microcapsule has a multi-layered (e.g., double-layered) microcapsule wall having an inner wall and an outer wall; the inner wall, encapsulating the active material, is formed of a silica polymer; and the outer wall, covering and in contact with the inner wall, is formed of a coacervate of gum arabic and gelatin.

Another aspect of this invention relates to a process of preparing any of the microcapsules described above. The process includes the steps of: (a) providing a sol-gel mixture that contains (i) a polysiloxane having a molecular weight of 1000-9000, (ii) gum arabic, (iii) gelatin, and (iv) a plurality of oil droplets dispersed in an aqueous phase, in which each of the oil droplets, having a size of 1 to 250 µm, contains an active material and a sol-gel precursor; (b) maintaining the pH value of the sol-gel mixture at 1 to 7 to obtain a microcapsule slurry; and (c) curing the microcapsule slurry, thereby obtaining a microcapsule of this invention.

The polysiloxane can be obtained by reacting water with a sol-gel precursor selected from a silica alkoxide monomer, or silica ester monomer, or alkoxysilanes monomer corresponding to the general formula: $(R_1O)(R_2O)Si(X)(X')$ wherein X is hydrogen, —$OR_3$, or $R_4$; and X' is hydrogen, —$OR_5$ or $R_6$; and each of $R_1$, $R_2$, $R_3$, $R_4$, $R_5$, and $R_6$, independently, is H, a linear, branched or cyclic alkyl group, or a linear, branched or cyclic siloxane group; and wherein the molar ratio between water and sol-gel precursor is 1:3 to 3:1.

Examples of the sol-gel precursor are tetramethyl orthosilicate, tetraethyl orthosilicate, a silica oligomer, and a combination thereof.

In some embodiments, the polysiloxane has the formula of: $(R_1O)[M(X)_a(X')_{2-a}O]_nR_2$, in which a is 0, 1 or 2, n is a integer from 100 to 1200, and each of $R_1$ and $R_2$, independently, is H or a $C_1$-$C_6$ alkyl (e.g., methyl, ethyl, n-propyl, isopropyl, n-butyl, n-pentyl, cylcopentyl, n-hexyl, cyclohexyl).

Another process of preparing the microcapsule include the steps of: (a) providing a sol-gel microcapsule mixture containing a plurality of microcapsules dispersed in an aqueous phase in the presence of a food-grade dispersant, in which each of the microcapsules has a microcapsule core and a microcapsule wall, the microcapsule core contains an active material, and the microcapsule wall is formed of a silica polymer; (b) adding gum arabic and gelatin to the sol-gel microcapsule mixture to obtain a microcapsule slurry; (c) maintaining the pH value of the microcapsule slurry at 1 to 6; and curing the microcapsule slurry, thereby obtaining a microcapsule of this invention.

Any process described above can further include the step of removing water from the microcapsule slurry to obtain the microcapsule in a solid form.

Also within the scope of this invention is a microcapsule composition prepared by any of the processes described above, either in a slurry or powder form.

Still within the scope of this invention is a consumer product containing any capsule described above. Examples of the consumer product are ingestible products for humans or animals selected from the group consisting of baked goods, dairy products, fruit ices, confectionery products, sugarless candies, jams, jellies, gelatins, puddings, animal feeds, pressed confectionery tablets, hard-boiled candies, pectin-based candies, chewy candies, creme-centered candies, fondants, sugarless hard-boiled candies, sugarless pectin-based candies, sugarless chewy candies, sugarless creme-centered candies, toothpastes, mouthwashes, breath fresheners, carbonated beverages, mineral waters, powdered beverage mixes, other non-alcoholic beverages, cough drops, lozenges, cough mixtures, decongestants, anti-irritants, antacids, anti-indigestion preparations and oral analgesics, chewing gums, and a cooling enhancing compositions.

Suitable consumer products also include liquid dish detergents, powder dish detergents, automatic dish detergents, laundry detergents, body wash, shampoos, hair conditioners, bar soap, liquid hand soap, all purpose cleaners, lip sticks, and kitchen cleaners.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The terms "capsule" and "microcapsule" herein are used interchangeably.

The term "alkyl" refers to a saturated, linear or branched hydrocarbon moiety, such as methyl, methylene, ethyl, ethylene, propyl, propylene, butyl, butylenes, pentyl, pentylene, hexyl, hexylene, heptyl, heptylene, octyl, octylene, nonyl, nonylene, decyl, decylene, undecyl, undecylene, dodecyl, dodecylene, tridecyl, tridecylene, tetradecyl, tetradecylene, pentadecyl, pentadecylene, hexadecyl, hexadecylene, heptadecyl, heptadecylene, octadecyl, octadecylene, nonadecyl, nonadecylene, icosyl, icosylene, triacontyl, and triacotylene.

The details of one or more embodiments of the invention are set forth in the description below. Other features, objects, and advantages of the invention will be apparent from the description and the claims.

DETAILED DESCRIPTION

It has been found that certain silica microcapsules showed unexpectedly high encapsulation efficiency and stability for delivering flavor in food products.

Some microcapsules of this invention have a size in the range of 0.01 to 1000 microns in diameter (e.g., 0.5 to 1000 microns, 1 to 200 microns, 0.5 to 150 microns, 1 to 100 microns, and 20 to 200 microns). The microcapsule size distribution can be narrow, broad, or multi-modal.

In some embodiments, the microcapsule has a microcapsule wall encapsulating a microcapsule core. The microcapsule core contains an active material, which is preferably a flavor. In addition, the active material can also be a fragrance, malodor counteractive agent, taste modulator, other active agent as those described below, or any combination thereof. The active material can be present at a level of 5 to 99% (preferably 20 to 95% and more preferably 40 to 90%) by weight of the microcapsule.

The microcapsule wall can be a single-layered or multi-layered. A single-layered microcapsule wall is formed of a first and second polymer. The first polymer is interlocked with the second polymer via covalent bonds, hydrogen bonds, dipolar interactions, or ionic interactions. A multi-layered microcapsule wall has at least a microcapsule inner wall and a microcapsule outer wall. The inner wall contacts and encapsulates the microcapsule core and is typically formed of a sol-gel polymer and a food-grade dispersant. The outer wall is typically formed of a hydrogel polymer, e.g., the coacervate of gum arabic and gelatin, the coacervate of purity gum ultra and chitosan, etc. The microcapsule wall can be present at a level of 1 to 95% with a lower limit of 1%, 5%, 10%, 20%, 30% and an upper limit of 95%, 80%, 70%, and 60%.

1. Sol-Gel Polymer

The sol-gel polymer is the polymerization product of a sol-gel precursor. The sol-gel precursors are compounds each capable of forming a sol-gel polymer. They are typically those containing silicon, boron, aluminum, titanium, zinc, zirconium, and vanadium. Preferred precursors are organosilicon, organoboron, organoaluminum including metal alkoxides and b-diketonates, and combinations thereof.

Sol-gel precursors suitable for the purposes of the invention are selected in particular from the group of di-, tri- and/or tetrafunctional silicic acids (including derivatives such as silicates), boric acids (including derivatives such as esters), and alumoesters, more particularly alkoxysilanes (alkyl orthosilicates), and precursors thereof.

One example of sol-gel precursors suitable for the purposes of the invention are compounds corresponding to the following general formula: $(R^1O)(R^2O)M(X)(X')$, wherein X can be hydrogen, $—OR^3$, or $R^4$; X' can be hydrogen, $—OR^5$, or $R^6$; and each of $R^1$, $R^2$, $R^3$, $R^4$, $R^5$, $R^6$ independently represent an organic group, more particularly a linear or branched alkyl group, preferably a $C_1$-$C_{12}$ alkyl. M can be Si, Ti, or Zr.

A preferred sol/gel precursor is alkoxysilanes corresponding to the following general formula: $(R^1O)(R^2O)Si(X)(X')$, wherein each of X, X', $R^1$, and $R^2$ are defined above.

Particularly preferred compounds are the silicic acid esters such as tetramethyl orthosilicate (TMOS) and tetraethyl orthosilicate (TEOS). A preferred compound includes Dynasylan® (organofunctional silanes commercially available from Degussa Corporation, Parsippany N.J., USA). Other sol-gel precursors suitable for the purposes of the invention are described, for example, in German Patent Application DE10021165. These sol-gel precursors are various hydrolyzable organosilanes such as, for example, alkylsilanes, alkoxysilanes, alkyl alkoxysilanes and organoalkoxysilanes. Besides the alkyl and alkoxy groups, other organic groups (for example allyl groups, aminoalkyl groups, hydroxyalkyl groups, etc.) may be attached as substituents to the silicon.

Recognizing that metal and semi metal alkoxide monomers (and their partially hydrolyzed and condensed polymers) such as TMOS, TEOS, etc. are very good solvents for numerous molecules and active ingredients is highly advantageous since it facilitates dissolving the active materials at a high concentration and thus a high loading in the final capsules.

Another class of sol-gel precursors are partially crosslinked silica, which is an oligomeric or polymeric silica having one or more (e.g., two or more) silicic acid functional groups such as silicic acid esters and alkoxysilane groups. Having these silicic acid functional groups, the partially crosslinked silica is capable of polymerizing with another sol-gel precursor and/or another partially crosslinked silica to form a sol-gel polymer, the microcapsule wall material that encapsulates an active material.

The partially crosslinked silica typically has a molecular weight less than 20,000 Da (e.g., 1,000 to 10,000 Da, 1,500 to 5,000 Da, and 2,000 to 3,500 Da).

The partially crosslinked silica can be prepared using an alkoxysilane described above. The alkoxysilane is polymerized to form oligomeric or polymeric silica having a molecular weight less than 20,000 Da. These partially crosslinked silica can then further polymerized to form a much larger sol-gel polymer to encapsulate an active material.

2. Food-Grade Dispersants

Turning to the food grade dispersants, they are added during the preparation of the microcapsule to form a stable emulsion (e.g., an oil-in-water emulsion). Oil droplets dispersed in a water phase in the emulsion contain an active material such as a flavor or modulator. A microcapsule wall formed of a silica polymer then encapsulates each of the oil droplets in the presence of the dispersant.

The food grade dispersants typically have an HLB of 1 to 20 (e.g., 1 to 16, 1 to 8, 4 to 8, 8 to 16, and 12 to 16). The term "HLB," as used herein, refers to the "hydrophilic-lipophilic balance" of a molecule. The HLB number indicates the polarity of the molecules in a range of 1-40, with the most commonly used emulsifiers having a value between 1 and 20. The HLB number increases with increasing hydrophilicity. The HLB of a surfactant can be determined by calculating values for the different regions of the molecule, as described by Griffin, "Classification of Surface-Active Agents by 'HLB,'" Journal of the Society of Cosmetic Chemists 1 (1949), 311-26; and Griffin, "Calculation of HLB Values of Non-Ionic Surfactants," Journal of the Society of Cosmetic Chemists 5 (1954), 249-56.

The term "food grade dispersant" refers to a dispersant having a quality as fit for human consumption in food. They can be natural or non-natural products. A natural product or surfactant refers to a product that is naturally occurring and comes from a nature source. Natural products/surfactants include their derivatives which can be salted, desalted, deoiled, fractionated, or modified using a natural enzyme or microorganism. On the other hand, a non-natural surfactant is a chemically synthesized surfactant by a chemical process that does not involve only an enzymatic modification.

Natural dispersants include quillaja saponin, lecithins, gum arabic, pectin, carrageenan, chitosan, chondroitin sulfate, cellulose gum, physically or enzymatically modified starch, whey protein, pea protein, egg white protein, silk protein, gelatin of fish, proteins of porcine or bovine origin, ester gum, fatty acids, and combinations thereof.

Quillaja saponin is a glucoside saponin contained in a Quallaja extract, which is obtained by aqueous extraction of the milled inner bark or branches of Quillaja saponaria, an evergreen tree in the family Quillajaceae. Quillaja saponins, having an average molecular weight of 1800-2000 Dalton, consist predominantly of glycosides (2-5 sugar units per each side chain) of quillaic acid. See Bomford et al., Vaccine 10, 572-77. They are non-ionic surfactants, resistant to salt and heat and stable to acid pH. Food-grade commercial products include Foamex Quillaja Saponaria (Garuda International, Exeter, Calif.) and Q-Naturale (Desert King International, Chile).

Lecithins may be native, deoiled (i.e., having 3% or less residual oil), fractionated (i.e., separating soluble components and insoluble components in a solvent, which can be an alcohol such as ethanol or an ethanol-water mixture), or enzyme modified (i.e., enzymatic hydrolysis of phospholipids, resulting in a higher polarity of the phospholipid molecules thereby enhancing lecithin's water solubility). A native lecithin (e.g., a standard fluid lecithin) has not been deoiled, fractioned, and/or enzymatically modified. An enzyme-modified lecithin (i.e., a lysolecithin) refers to a class of compounds each of which has a partial hydrolysis product of a phosphatidylcholine resulting from removing one of the two fatty acid groups from the phosphatidylcholine.

Gum arabic is a natural gum made of the hardened sap of acacia trees, e.g., Senegalia (Acacia) senegal and Vachellia (Acacia) seyal, two species historically cultivated in Arabia and West Asia. Gum arabic is a complex mixture of glycoproteins and polysaccharides. It is edible and used primarily in the food industry as a stabilizer, binder, thickening agent, and viscosity control agent. Gum arabic is commercially available from many suppliers such as Nexira (Rouen, France) and TIC Gums Inc. (White Marsh, Md.).

Pectin consists of a set of polysaccharides that are present in the primary cell walls of terrestrial plants. Produced commercially as a white to light brown powder, it is mainly extracted from citrus fruits, and is used in food as a gelling agent, thickening agent, stabilizer, and dietary fiber. Pectin is available in different grades from suppliers such as Cargill Inc. (Minneapolis, Minn.) and Pacific Pectin Inc. (Oakhurst, Calif.).

Carrageenans are a family of linear sulfated polysaccharides that are extracted from red edible seaweeds. They are widely used in the food industry as a gelling agent, thickening agent, and stabilizer. There are three main varieties of carrageenan, which differ in their degree of sulfation. Kappa-carrageenan has one sulfate group per disaccharide. Iota-carrageenan has two sulfates per disaccharide. Lambda carrageenan has three sulfates per disaccharide. Any one of these three varieties can be used in this invention. Carrageenan is commercially available from many suppliers such as Cargill Inc. (Minneapolis, Minn.) and Pacific Pectin Inc. (Oakhurst, Calif.).

Chitosan is a linear polysaccharide composed of randomly distributed α-(1-4)-linked D-glucosamine (deacetylated unit) and N-acetyl-D-glucosamine (acetylated unit). It is made by treating shrimp and other crustacean shells with the alkali sodium hydroxide. Chitosan has been used in food and medicine as a dietary fiber, fining agent, and antibacterial agent. Commercially suppliers include Parchem (New Rochelle, N.Y.) and G.T.C. Bio Corp. (Shangdong, China).

Chondroitin sulfates are made from extracts of cartilages from animals such as cows, pigs, sharks and other fish, and birds. They are sulfated glycosaminoglycans (GAG) composed of a chain of alternating sugars (N-acetylgalactosamine and glucuronic acid), usually found attached to proteins as part of a proteoglycan. A chondroitin chain can have over 100 individual sugars, each of which can be sulfated in variable positions and quantities. Based on the site of sulfation, Chondroitin sulfates exist as four major forms: Chondroitin sulfate (i.e., chondroitin-4-sulfate A), sulfated on carbon 4 of the N-acetylgalactosamine (GalNAc) sugar; Chondroitin sulfate C (i.e., chondroitin-6-sulfate), sulfated on carbon 6 of the GalNAc sugar; Chondroitin sulfate D (i.e., chondroitin-2,6-sulfate), sulfated on carbon 2 of the glucuronic acid and 6 of the GalNAc sugar; and Chondroitin sulfate E (i.e., chondroitin-4,6-sulfate), sulfated on carbons 4 and 6 of the GalNAc sugar. Any one or combination of the four forms can be used in this invention. Chondroitin sulfates are commercially available from suppliers such as Summit Nutritionals International Inc. (Branchburg, N.J.). These compounds have been widely used as dietary supplements especially for treatment of osteoarthritis.

Whey protein, pea protein, egg white protein, silk protein, and proteins of porcine or bovine origin are extracted from whey, yellow pea, egg white, silk, pork, and beef respectively. They are commercially available such as Barflex Whey Protein by Glanbia Nutritionals (Fitchburg, Wis.), Veg-O-Tein Pea Protein Powder by Axiom Foods Inc. (Los Angeles, Calif.), Jay Robb Unflavored Egg White Protein by Jay Robb Enterprises Inc. (Carlsbad, Calif.), and Aotesi Silk Powder by Aotesi Biochemical (Huzhou, China).

Fatty acids are carboxylic acids with a long aliphatic chain, which is either saturated or unsaturated. They can be natural or synthetic. Most naturally occurring fatty acids have an unbranched chain and a number of carbon atoms from 4 to 28. Suitable fatty acids include short-chain fatty acids (having fewer than six carbons, e.g., butyric acid), medium-chain fatty acids (having 6-12), long-chain fatty acids (having 13-21 carbons), very long chain fatty acids (having 22 or more carbons), saturated fatty acids, unsaturated fatty acids (having one or more carbon-carbon double bonds including trans and cis isomers), Examples are α-Linolenic acid, stearidonic acid, eicosapentaenoic acid, docosahexaenoic acid, linoleic acid, γ-linolenic acid, dihomo-γ-linolenic acid, arachidonic acid, docosatetraenoic acid, palmitoleic acid, vaccenic acid, paullinic acid, oleic acid, elaidic acid, gondoic acid, erucic acid, nervonic acid, mead acid, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, octatriacontanoic acid, animal fats (e.g., lard, duck fat, and butter), and vegetable fats (e.g., coconut oil, cocoa butter, palm kernel oil, palm oil, cottonseed oil, wheat germ oil, soybean oil, olive oil, corn oil, sunflower oil, safflower oil, hemp oil, and canola/rapeseed oil). There are many suppliers for fatty acids, such as Chemical Associates Inc. (Copley, Ohio), VVF North America (Kansas City, Kans.), and Parchem Fine and Specialty Chemicals (New Rochelle, N.Y.).

Gelatin is a translucent, colorless, brittle (when dry), flavorless food derived from collagen obtained from various animal (e.g., fish) by-products. It is commonly used as a gelling agent in the food and pharmaceutical industry. Gelatin is an irreversibly hydrolyzed form of collagen. It is found in most gummy candy, as well as other products such as marshmallows, gelatin desserts, and some ice creams, dips, and yogurts.

Non-natural dispersants include N-lauroyl-L-arginine ethyl ester, sorbitan esters, polyethoxylated sorbitan esters, polyglyceryl esters, fatty acid esters, cellulose gum, and ester gum. N-lauroyl-L-arginine ethyl ester is typically synthesized by esterifying arginine with ethanol, followed by reacting the ester with lauroyl chloride. Most commercially products are available as a hydrochloride salt. N-lauroyl-L-arginine ethyl ester has a molecular weight of 421 and a water solubility greater than 247 g/kg in water at 20° C.

Sorbitan esters (also known as Spans) are nonionic surfactants for food and pharmaceutical use. Examples include sorbitan monolaurate (i.e., Span 20), sorbitan monopalmitate (i.e., Span 40), sorbitan monostearate (i.e., Span 60), sorbitan tristearate (i.e., Span 65), sorbitan monooleate (i.e., Span 80), sorbitan sesquioleate (i.e., Span 83), sorbitan trioleate (i.e., Span 85), and sorbitan isostearate (i.e., Span 120). They are commercially available from Croda Inc. (Edison, N.J.) under the Anfomul™, Atmer™, Crill™, Span™ and Vykamol™ product lines.

Suitable polyethoxylated sorbitan fatty acid esters include polyoxyethylene sorbitan monolaurate, polyoxyethylene sorbitan monopalmitate, polyoxyethylene sorbitan monostearate, and polyoxyethylene sorbitan monooleate. The number of repetitive oxyethylene —($CH_2CH_2$—O)— can be in the range of 2 to 1000 (e.g., 5 to 100, 10 to 50, 10 to 30, and 20). Commercially available polyethoxylated sorbitan fatty acid esters are those under the name Tween™ by ICI Americas, Inc. (Wilmington, Del.), e.g., Tween™ 40 (polyoxyethylene sorbitan monopalmitate), Tween™ 60 (polyoxyethylene sorbitan monostearate, HLB of 14.9), Tween™ 80 (polyoxyethylene sorbitan monooleate, HLB of 15), and Tween™ 20 (polyoxyethylene sorbitan monolaurate, HLB of 16.7). They have 20 repetitive oxyethylene units.

Polyglyceryl esters are formed chemically by esterification of fatty acids to one or several hydroxyl groups of polyglycerol. These polyglycerols can contain two to ten glycerol moieties, e.g., diglycerol, triglycerol, tetraglycerol, dodeglycerol, and the like. Typically, 30 to 50% of the hydroxyl groups are esterified by fatty acids. These fatty acids are formed either of one species (lauric, stearic, oleic acid, coconut fatty acids) or a mixture from vegetal oils (corn oil, cottonseed oil, lard, palm oil, peanut oil, safflower oil, sesame oil, soybean oil, or castor oil) or from animal source (beeswax). Polyglyceryl esters are used as non-ionic surfactants in cosmetic, food, and pharmaceutical industries. They have been used as emulsifying agents in the production of fine bakery and chewing gum.

Glycerol ester of wood rosin, i.e., ester gum, is an oil-soluble food additives used in foods, beverages, and cosmetics to keep oils in suspension in water. It is also used as an ingredient in the production of chewing-gum and ice cream.

Fatty acid esters are prepared from a fatty acid and an alcohol. When the alcohol component is glycerol, the fatty acid esters produced can be monoglycerides, diglycerides, or triglycerides. Other alcohol components include simple alcohols (e.g., methanol, ethanol, and propanol), sugar alcohol (e.g., erythritol, threitol, arabitol, xylitol, ribitol, mannitol, sorbitol, galactitol, fucitol, iditol, inositol, volemitol, isomalt, maltitol, lactitol, maltotriitol, and maltotetraitol), and other polyol (e.g., ethylene glycol). The fatty acid component can be selected from any of the fatty acids described above.

Cellulose gum, i.e., carboxylmethyl cellulose, can have a molecular weight range between 90,000 Daltons to 1,500,000 Daltons, preferably between 250,000 Daltons to 750,000 Daltons and more preferably between 400,000 Daltons to 750,000 Daltons. In some embodiments, the cellulose gum has a degree of substitution between 0.1 to 3, preferably between 0.65 to 1.4, and more preferably between 0.8 to 1. The term "cellulose gum" as used herein includes its derivative such as alkyl-substituted cellulose (e.g., methylcellulose ad ethylcellulose commercially available from DOW Corporation), hydroxyethyl cellulose, hydroxypropyl celluloses (KLUCEL polymers commercially available from Hercules), and cellulose acetate butyrate (commercially available from Eastman Chemical).

Other food safe dispersant can also be included in the microcapsule of this invention. Examples include ammonium phosphatides, acetic acid esters of mono- and diglycerides (Acetem), lactic acid esters of mono- and diglycerides of fatty acids (Lactem), citric acid esters of mono and diglycerides of fatty acids (Citrem), mono and diacetyl tartaric acid esters of mono and diglycerides of fatty acids (Datem), succinic acid esters of monoglycerides of fatty acids (SMG), ethoxylated monoglycerides, sucrose esters of fatty acids, sucroglycerides, polyglycerol polyricinoleate, propane-1,2-diol esters of fatty acids, thermally oxidized soya bean oil interacted with mono- or diglycerides of fatty acids, sodium stearoyl lactylate (SSL), calcium stearoyl lactylate (CSL), stearyl tartrate, polyglycerol esters of interesterified castor oil acid (E476), sodium stearoyllatylate, sodium lauryl sulfate, polyoxyethylated hydrogenated castor oil (for instance, such sold under the trade name CREMOPHOR), block copolymers of ethylene oxide and propylene oxide (for instance as sold under the trade name PLURONIC or the trade name POLOXAMER), polyoxyethylene fatty alcohol ethers, and polyoxyethylene stearic acid ester.

The above described dispersant can be used alone or in any combination at any ratio. The amount of these dispersant is anywhere from 0.1 to 40 percent by weight of the microcapsule, more preferably from 0.5 to 10 percent, more preferably 0.5 to 5 percent by weight.

3. Second Polymers

In some embodiments, the microcapsule of this invention has a microcapsule outer wall that coats and is in contact with the microcapsule inner wall.

The microcapsule outer wall is formed of a second polymer. Suitable second polymers are those compatible with the sol-gel polymers in the inner wall. One particular group of polymers useful for forming the outer wall are hydrogels, namely, Hydrogels are commonly accepted to be materials consisting of a permanent, three-dimensional network of hydrophilic polymers with water filling the space between the polymer chains. Examples include gum arabic, purity gum ultra, gelatin, chitosan, xanthan gum, plant gum, carboxymethyl cellulose, sodium carboxymethyl guar gum, and combinations thereof. Preferred polymers are the coacervate of gum arabic and gelatin, and the coacervate of purity gum ultra and chitosan.

4. Single-Layered Microcapsules

In some embodiments, the microcapsule of this invention is a single-layered microcapsule having a microcapsule wall formed of a first polymer and a second polymer. The first and second polymers can those described above. These two polymers are interlocked and interweaved with each other to form a polymeric network as the microcapsule wall.

The microcapsules thus prepared can be used as free microcapsules or in aggregates in a slurry or solid form. In some embodiments, the aggregate is formed using an aggregate formation aid. Suitable aggregate formation aids include water-soluble cations, water-soluble anions, and a transglutaminase. Preferred aggregate formation aids are the transglutaminase, multivalent water-soluble anions (e.g., sulfate, carbonate, and phosphate) and anionic polymers (such as an alginate, poly(styrene sulfonate), hyaluronic acid, poly(acrylic acid), carboxymethylecellulose, gelatin, and combinations thereof).

Encapsulation Methods

Conventional encapsulation methods can be used to prepare the silica microcapsules. See WO 2015023961.

By way of illustration, to prepare a silica microcapsule, a sol-gel emulsion is first obtained by emulsifying an oil phase into an aqueous phase in the presence of a food-grade dispersant. The sol-gel emulsion thus prepared has a plurality of oil droplets dispersed in the aqueous phase, in which each of the oil droplets has a size of 1 to 1000 μm and contains an active material, and the aqueous phase contains a sol-gel precursor. The pH value of the sol-gel emulsion is maintained at 1 to 7. In some embodiments, a food-grade acid or base is added to the emulsion to adjust the pH value to the desired level. The polymerization of the sol-gel precursor into a sol-gel polymer leads to the formation of a plurality of microcapsules. In accordance with some embodiments of this invention, the microcapsules prepared according to the methods above are cured at a temperature in the range of 15-230° C. (e.g., 15-135° C., 20-90° C., 15-55° C., 55-95° C., 35-65° C., 65-110° C., 55-75° C., and 90-130° C.) for 1 minute to 24 hours (e.g., 0.1 hours to 5 hours, 0.2 hours to 4 hours and 0.5 hours to 3 hours). A skilled person in the art can determine, without undue experiments, the curing temperature, duration, and the heating rate.

To obtain microcapsules with more leaching of the active material, certain embodiments of this invention provide for a cure at a low temperature, e.g., less than 100° C. In some embodiments, the cure temperature is at or less than 90° C. In other embodiments, the cure temperature is at or less than 80° C. (e.g., 5 to 75° C., 10 to 50° C., 15 to 45° C., and 20 to 35° C.).

In one embodiment, the capsules are heated to a target cure temperature at a linear rate of 0.5 to 2° C. per minute (e.g., 1 to 5° C. per minute, 2 to 8° C. per minute, and 2 to 10° C. per minute) over a period of 1 to 60 minutes (e.g., 1 to 30 minutes). The following heating methods may be used: conduction for example via oil, steam radiation via infrared, and microwave, convection via heated air, steam injection and other methods known by those skilled in the art. The target cure temperature used herein refers to the minimum temperature in degrees Celsius at which the capsules may be cured to retard leaching.

Other Delivery Systems

The silica microcapsule compositions described above can also include one or more addition delivery systems.

In some embodiments, the silica microcapsule contains one or more additional microcapsules having a microcapsule wall formed of melamine formaldehyde, polyurethane, polysiloxanes, polyurea, polyamide, polyimide, polyvinyl alcohol, polyanhydride, polyolefin, polysulfone, polysaccharide, protein, polylactide (PLA), polyglycolide (PGA), polyorthoester, polyphosphazene, silicone, lipid, modified cellulose, gums, polystyrene, and polyesters or combinations of these materials. Other polymeric materials that are functional are ethylene maleic anhydride copolymer, styrene maleic anhydride copolymer, ethylene vinyl acetate copolymer, and lactide glycolide copolymer. Biopolymers that are derived from alginate, chitosan, collagen, dextran, gelatin, and starch can also be used as the encapsulating materials. Additionally, capsules can be made via the simple or complex coacervation of gelatin. Other suitable encapsulating wall polymers include those formed from isocyanates, acrylates, acrylamide, acrylate-co-acrylamide, hydrogel monomers, sol-gel precursors, gelatin, melamine-formaldehyde or urea-formaldehyde condensates, as well as similar types of aminoplasts. See WO 2016049456.

The capsule delivery system can also contain one or more other delivery system such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof. More exemplary delivery systems that can be incorporated are coacervate capsules, cyclodextrin delivery systems, and pro-perfumes.

Active Materials

The core of the capsules of the invention can include one or more active materials including, but not limited to, flavors and/or fragrance ingredients such as fragrance oils. Individual active materials that can be encapsulated include those listed in WO 2016049456, pages 38-50. These active material include flavor or fragrance ingredients, taste masking agents, taste sensates, malodor counteracting agents, vitamins, antibacterials, sunscreen actives, antioxidants, anti-inflammatory agents, anesthetics, analgesics, antifungal agents, antibiotics, anti-viral agents, anti-parasitic agents, anti-infectious and anti-acne agents, dermatological active ingredients, enzymes and co-enzymes, skin whitening agents, anti-histamines, chemotherapeutic agents, and insect repellents.

In addition to the active materials listed above, the products of this invention can also contain, for example, the following dyes, colorants or pigments: lactoflavin (riboflavin), beta-carotene, riboflavin-5'-phosphate, alpha-carotene, gamma-carotene, cantaxanthin, erythrosine, curcumin, quinoline yellow, yellow orange S, tartrazine, bixin, norbixin (annatto, orlean), capsanthin, capsorubin, lycopene, beta-apo-8'-carotenal, beta-apo-8'-carotenic acid ethyl ester, xantophylls (flavoxanthin, lutein, cryptoxanthin, rubixanthin, violaxanthin, rodoxanthin), fast carmine (carminic acid, cochineal), azorubin, cochineal red A (Ponceau 4 R), beetroot red, betanin, anthocyanins, amaranth, patent blue V, indigotine I (indigo-carmine), chlorophylls, copper compounds of chlorophylls, acid brilliant green BS (lissamine green), brilliant black BN, vegetable carbon, titanium dioxide, iron oxides and hydroxides, calcium carbonate, aluminum, silver, gold, pigment rubine BK (lithol rubine BK), methyl violet B, victoria blue R, victoria blue B, acilan brilliant blue FFR (brilliant wool blue FFR), naphthol green B, acilan fast green 10 G (alkali fast green 10 G), ceres yellow GRN, sudan blue II, ultramarine, phthalocyanine blue, phthalocayanine green, fast acid violet R. Further naturally obtained extracts (for example paprika extract, black carrot extract, red cabbage extract) can be used for coloring purposes. Goods results are also achieved with the colors named in the following, the so-called aluminum lakes: FD & C Yellow 5 Lake, FD & C Blue 2 Lake, FD & C Blue 1 Lake, Tartrazine Lake, Quinoline Yellow Lake, FD & C Yellow 6 Lake, FD & C Red 40 Lake, Sunset Yellow Lake, Carmoisine Lake, Amaranth Lake, Ponceau 4R Lake, Erythrosyne Lake, Red 2G Lake, Allura Red Lake, Patent Blue V Lake, Indigo Carmine Lake, Brilliant Blue Lake, Brown HT Lake, Black PN Lake, Green S Lake and mixtures thereof.

When the active material is a fragrance, it is preferred that fragrance ingredients within a fragrance having a C log P of 0.5 to 15 are employed. For instance, the ingredients having a C log P value between 0.5 to 8 (e.g., between 1 to 12, between 1.5 to 8, between 2 and 7, between 1 and 6, between 2 and 6, between 2 and 5, between 3 and 7) are 25% or greater (e.g., 50% or greater, 60% or greater, 80% or greater, and 90% or greater) by the weight of the fragrance.

In some embodiments, it is preferred that a fragrance having a weight-averaged C log P of 2.5 and greater (e.g., 3 or greater, 2.5 to 7, and 2.5 to 5) is employed. The weight-averaged C log P is calculated as follows:

$$C \log P = \{\text{Sum}[(W_i)(C \log P)_i]\}/\{\text{Sum } W_i\},$$

in which $W_i$ is the weight fraction of each fragrance ingredient and $(C \log P)_i$ is the C log P of that fragrance ingredient.

In some embodiments, the amount of encapsulated active material is from 5 to 95% (e.g., 20 to 90% and 40 to 85%) by weight of the capsule. The amount of the capsule wall is from 0.5% to 25% (e.g., 1.5 to 15% and 2.5 to 10%) also by weight of the capsule. In other embodiments, the amount of the encapsulated active material is from 15% to 99.5% (e.g., 50 to 98% and 30 to 95%) by weight of the capsule, and the amount of the capsule wall is from 0.5% to 85% (e.g., 2 to 50% and 5 to 70%) by weight of the capsule.

Adjunct Materials

In addition to the active materials, the present invention also contemplates the incorporation of adjunct materials including solvent, emollients, and core modifier materials in the core encapsulated by the capsule wall. Other adjunct materials are solubility modifiers, density modifiers, stabilizers, viscosity modifiers, pH modifiers, or any combination thereof. These modifiers can be present in the wall or core of the capsules, or outside the capsules in delivery system. Preferably, they are in the core as a core modifier.

The one or more adjunct material may be added in the amount of from 0.01% to 25% (e.g., from 0.5% to 10%) by weight of the capsule.

Suitable examples include those described in US 2016/0158121, pages 15-18.

Deposition Aids

A capsule deposition aid from 0.01 to 25%, more preferably from 5 to 20% can be included by weight of the capsule. The capsule deposition aid can be added during the preparation of the capsules or it can be added after the capsules have been made.

A capsule deposition aid from 0.01 to 25%, more preferably from 5 to 20% can be included by weight of the capsule. The capsule deposition aid can be added during the preparation of the capsules or it can be added after the capsules have been made.

These deposition aids are used to aid in deposition of capsules to surfaces such as fabric, hair or skin. These include anionically, cationically, nonionically, or amphoteric water-soluble polymers.

Suitable deposition aids include polyquaternium-4, polyquaternium-5, polyquaternium-6, polyquaternium-7, polyquaternium-10, polyquaternium-16, polyquaternium-22, polyquaternium-24, polyquaternium-28, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, an acrylamidopropyltrimonium chloride/acrylamide copolymer, a methacrylamidopropyltrimonium chloride/acrylamide copolymer, and combinations thereof. Other suitable deposition aids include those described in WO 2016049456, pages 13-27; US 20130330292; US 20130337023; and US 20140017278.

Capsule Delivery System

The microcapsule of this invention can be formulated into a capsule delivery system (e.g., a microcapsule composition) for use in consumer products.

(i) Slurry. The capsule delivery system can be a slurry containing in a solvent (e.g., water) the capsule at a level 0.1 to 80% (preferably 1 to 65% and more preferably 5 to 45%) by weight of the capsule delivery system.

(ii) Spray drying. The delivery system can also be spray dried to a solid form. In a spray drying process, a spray dry carrier is added to a capsule delivery system to assist the removal of water from the slurry.

According to one embodiment, the spray dry carriers can be selected from the group consisting of carbohydrates such as chemically modified starches and/or hydrolyzed starches, gums such as gum arabic, proteins such as whey protein, cellulose derivatives, clays, synthetic water-soluble polymers and/or copolymers such as polyvinyl pyrrolidone, polyvinyl alcohol. The spray dry carriers may be present in an amount from 1 to 50%, more preferably from 5 to 20%.

Optionally, a free flow agent (anticaking agent) of silicas which may be hydrophobic (i.e. silanol surface treated with halogen silanes, alkoxysilanes, silazanes, siloxanes, etc. such as Sipernat D 17, Aerosil R972 and R974 (available from Degussa), etc.) and/or hydrophilic such as Aerosil 200, Sipernat 22S, Sipernat 50S, (available from Degussa), Syloid 244 (available from Grace Davison), may be present from 0.01 to 10%, more preferable from 0.5 to 5%.

Humectants and viscosity control/suspending agents can also be added to facilitate spray drying. These agents are disclosed in U.S. Pat. Nos. 4,428,869, 4,464,271, 4,446,032, and 6,930,078. Details of hydrophobic silicas as a functional delivery vehicle of active materials other than a free flow/anticaking agent are disclosed in U.S. Pat. Nos. 5,500,223 and 6,608,017.

The spray drying inlet temperature is in the range of 150 to 240° C., preferably between 170 and 230° C., more preferably between 190 and 220° C.

(iii) Other drying methods. A solid and/or powdered capsules can also be obtained through filtration, air drying, belt drying, vacuum drying, freeze drying, drum drying, and any combination thereof.

(iv) Additional components. The capsule delivery system can include one or more non-confined/unencapsulated active materials from 0.01% to 50%, more preferably from 5% to 40%.

More examples include those described in US 2016/0158121, pages 24 to 25.

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethylammonium ion). A precursor can be ester and another suitable derivative, which, during the process of preparing a polyurea or polyurethane capsule composition of this invention, is capable of converting to the compound, polymer, or agent and being used in preparing the polyurea or polyurethane capsule composition. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine.

Certain compounds, polymers, and agents have one or more stereocenters, each of which can be in the R configuration, the S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof.

Flavors often contain both hydrophilic and lipophilic ingredients. Hydrophilic ingredients are water soluble and/or volatile, which are more prone to loss during the encapsulation process. It is sometimes advantageous to divide the flavor into hydrophilic and lipophilic portions, and encapsulate each portion with different encapsulation technologies, and combine these encapsulated portions at the appropriate ratio in the final consumer products.

The lipophilic portion is encapsulated as described in above, and the hydrophilic portion is encapsulated with other methods such as spray dry, extrusion, spray chill, etc., or as a non-encapsulated oil. The hydrophilic and lipophilic encapsulations are mixed in an appropriate ratio in consumer products such as snacks, cakes, cookies, crackers, chips, marinades, etc.

Alternatively, the hydrophilic portion of a flavor is encapsulated using the process described above. This microcapsule is then mixed with the original flavor which could be in any form such as microcapsules, spray dried, extrusion, spray chilled, and non-encapsulated oil, in an appropriate ratio in the final consumer products.

Encapsulating lipophilic and hydrophilic flavor portions separately will avoid the loss of either portion during the encapsulating process.

Applications.

The microcapsules and delivery systems of the present invention are well-suited for use, without limitation, in the following products: household products including Liquid or Powder Laundry Detergents, unit dose pouches, tablets and capsules, scent boosters, fabric care products such as rinse conditioners (containing 1 to 30 weight % of a fabric conditioning active), fabric liquid conditioners (containing 1 to 30 weight % of a fabric conditioning active), tumble drier sheets, fabric refreshers, fabric refresher sprays, ironing liquids, and fabric softener systems, liquid fabric softeners/fresheners, liquid dish detergents such as those described in U.S. Pat. Nos. 6,069,122 and 5,990,065, automatic dish detergents, all-purpose cleaners including bucket dilutable cleaners and toilet cleaners, bathroom cleaners, bath tissues, rug deodorizers, candles, room deodorizers, floor cleaners, disinfectants, window cleaners, garbage bags/trash can liners, air fresheners including room deodorizer and car deodorizer, scented candles, sprays, scented oil air freshener, automatic spray air freshener, and neutralizing gel beads, moisture absorber, household devices such as paper towels and disposable wipes, moth balls/traps/cakes, baby care products, diaper rash cream/balm, baby powder, baby care devices, diapers, bibs, wipes, oral care products, tooth care products, oral care products (abrasive or polishing agent, for example silicic acids, calcium carbonates, calcium phosphates, aluminum oxides and/or hydroxylapatites; surface-active substances, for example sodium lauryl sulfate, sodium lauryl sarcosinate and/or cocamidopropylbetaine; humectants, for example glycerol and/or sorbitol; thickening agents, for example carboxymethyl cellulose, polyethylene glycols, carrageenan and/or Laponite™; sweeteners, for example saccharin; taste correctors for unpleasant taste sensations, taste correctors for further, normally not unpleasant taste sensations; taste-modulating substances, for example inositol phosphate, nucleotides such as guanosine monophosphate, adenosine monophosphate or other substances such as sodium glutamate or 2-phenoxypropionic acid; cooling active ingredients, for example menthol derivatives, including L-menthyllactate, L-menthylalkylcarbonates, menthone ketals, menthane carboxylic acid amides, 2,2,2-trialkylacetic acid amides including 2,2-diisopropylpropionic acid methyl amide, icilin and icilin derivatives; stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors), tooth paste (an exemplary formulation as follows: calcium phosphate 40-55%, carboxymethyl cellulose 0.8-1.2%, sodium lauryl sulfate 1.5-2.5%, glycerol 20-30%, saccharin 0.1-0.3%, flavor oil 1.0-2.5%, water q.s. to 100%, all by weight of the tooth paste formulation), tooth powder, oral rinse, tooth whiteners, denture adhesive, health care devices including dental floss, toothbrushes, respirators, scented/flavored condoms, feminine hygiene products such as tampons, feminine napkins and wipes, and pantiliners, personal care products: cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a Phase Inversion Temperature ("PIT") emulsion, a Pickering emulsion, a micro-emulsion or nano-emulsion; and emulsions which are particularly preferred are of the "oil-in-water" (O/W) type or water-in-oil-in-water (W/O/W) type. More specifically, personal cleansers (bar soaps, body washes, and shower gels), in-shower conditioner, sunscreen ant tattoo color protection (sprays, lotions, and sticks), insect repellants, hand sanitizer, antiinflammatory balms, ointments, and sprays, antibacterial ointments and creams, sensates, deodorants and antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deodorant, wax-based deodorant, glycol/soap type deodorant, lotion including body lotion, facial lotion, and hand lotion, body powder and foot powder, toiletries, body spray, shave cream and male grooming products, bath soak, exfoliating scrub, personal care devices, facial tissues, cleansing wipes, hair care products, shampoos (liquid and dry powder), hair conditioners (rinse-out conditioners, leave-in conditioners, and cleansing conditioners, hair rinses, hair refreshers, hair perfumes, hair straightening products, hair styling products, hair fixative and styling aids, hair combing creams, hair wax, hair foam, hair gel, nonaerosol pump spray, hair bleaches, dyes and colorants, perming agents, hair wipes, beauty care products, fine fragrance—alcoholic, solid perfume, lipstick/lip balm, make-up cleanser, skin care cosmetic such as foundation, pack, sunscreen, skin lotion, milky lotion, skin cream, emollients, skin whitening, make-up cosmetic including manicure, mascara, eyeliner, eye shadow, liquid foundation, powder foundation, lipstick and cheek rouge, consumer goods packaging such as fragranced cartons, fragranced plastic bottles/boxes, pet care products, cat litter, flea and tick treatment products, pet grooming products, pet shampoos, pet toys, treats, and chewables, pet training pads, pet carriers and crates, confectionaries confectionery, preferably selected from the group consisting of chocolate, chocolate bar products, other products in bar form, fruit gums, hard and soft caramels and chewing gum (gum base (natural latex chicle gum, most current chewing gum bases also presently include elastomers, such as polyvinylacetate (PVA), polyethylene, (low or medium molecular weight) polyisobutene (PIB), polybutadiene, isobutene-isoprene copolymers (butyl rubber), polyvinylethylether (PVE), polyvinylbutyether, copolymers of vinyl esters and vinyl ethers, styrene-butadiene copolymers (styrene-butadiene rubber, SBR), or vinyl elastomers, for example based on vinylacetate/vinyllaurate, vinylacetate/vinylstearate or ethylene/vinylacetate, as well as mixtures of the mentioned elastomers, as described for example in EP 0 242 325, U.S. Pat. Nos. 4,518,615, 5,093,136, 5,266,336, 5,601,858 or U.S. Pat. No. 6,986,709.) 20-25%; powdered sugar 45-50%; glucose 15-17%; starch syrup 10-13%; plasticizer 0.1%; flavor 0.8-1.2%; the components described above were kneaded by a kneader according to the foregoing formulation to provide a chewing gum. Encapsulated Flavor or sensate is then added and blended till homogeneous), breath fresheners, orally dissolvable strips, chewable candy, hard candy, baked products, preferably selected from the group consisting of bread, dry biscuits, cakes and other cookies, snack foods, preferably selected from the group consisting of baked or fried potato chips or potato dough products, bread dough products and corn or peanut-based extrudates; potato, tortilla, vegetable or multigrain chips, popcorn, pretzels, extruded stacks, cereal products preferably selected from the group consisting of breakfast cereals, muesli bars and precooked finished rice products, alcoholic and non-alcoholic beverages, preferably selected from the group consisting of coffee, tea, wine, beverages containing wine, beer, beverages containing beer, liqueurs, schnapps, brandies, sodas containing fruit, isotonic beverages, soft drinks, nectars, fruit and vegetable juices and fruit or vegetable preparations; instant beverages, preferably selected from the group consisting of instant cocoa beverages, instant tea beverages and instant coffee beverages, ready to drink liquid drinks, liquid drink concentrates, powder drinks, coffee such as instant cappuccino, tea, alcoholic, spice blends and consumer prepared foods, powder gravy, sauce mixes, condiments, fermented products, ready to heat foods (ready meals and soups, preferably selected from the group consisting of powdered soups, instant soups, precooked soups, sauces, stews, frozen entrees), dairy products milk products, preferably selected from the group consisting of milk beverages, ice milk, yogurt, kefir, ice cream, cheese, cream cheese, soft cheese, hard cheese, powdered milk, whey, butter, buttermilk, bean curd, and partially or fully hydrolyzed milk protein-containing products, flavored milk beverages, soya protein or other soybean fractions, preferably selected from the group consisting of soya milk and products produced therefrom, soya lecithin-containing preparations, fermented products such as tofu or tempeh or products produced therefrom and soy sauces, meat products, preferably selected from the group consisting of ham, fresh or raw sausage preparations, and seasoned or marinated fresh or salt meat products, eggs or egg products, preferably selected from the group consisting of dried egg, egg white and egg yolk, oil-based products or emulsions thereof, preferably selected from the group consisting of mayonnaise, remoulade, dressings and seasoning preparations, fruit preparations, preferably selected from the group consisting of jams, sorbets, fruit sauces and fruit fillings; vegetable preparations, preferably selected from the group consisting of ketchup, sauces, dried vegetables, deep-frozen vegetables, precooked vegetables, vegetables in vinegar and preserved vegetables, and flavored pet foods.

These applications are all well-known and described in WO 2016/049456, pages 60-70.

The invention is described in greater detail by the following non-limiting examples. Without further elaboration, it is believed that one skilled in the art can, based on the description herein, utilize the present invention to its fullest extent. All publications cited herein are incorporated by reference in their entirety.

Example 1

A silica microcapsule of this invention, i.e., Microcapsule 1, is prepared following the procedure below.

Tetraethyl orthosilicate (TEOS) (commercially available from Evonik Corporation, Piscataway, N.J.) 40 g was added to 36 g 0.01 N hydrochloric acid and the mixture was stirred at 45° C. for 30 minutes. Additional 376 g TEOS was added dropwise during 1 hour. The mixture was stirred at 45° C. 16 hours, and loaded into a Rotavapor to remove lights with the aid of 10 mmHg vacuum. The resulting 275 g colorless liquid polysiloxane material (Poly-Si) was saved and used in capsule preparation. The polysiloxane materials thus prepared have a viscosity of 5-30 (Brookfield DV1 viscometer, 60 rpm, ambient temperature, spindle 4), and a molecular weight of between 1000 and 3000.

A solution of 2 g gelatin A (commercially available from Great Lakes Gelatin Co., Grayslake, Ill.) in 118 g of water was heated to 50° C. Gum Arabic (2 g) was added as a 10% aqueous solution (20), followed by the addition of 40 g of mint oil in 10 g of pretreated silica Poly-Si. The pH was adjusted to 4.5 with 10% acetic acid solution. The resultant mixture was stirred with an overhead stirrer at 600 rpm and cooled slowly to room temperature (20° C.). Consequently, to the mixture was added a solution of 6 g of sodium silicate (37.5% aqueous solution, commercially available from PQ Corp., Malvern, Pa.) in 80 g of water. After the pH was adjusted to 6.6, the resultant mixture was stirred for 1 hour at room temperature to obtain Microcapsule 1. The amount of precursor (e.g., pretreated silica Poly-Si as used in this example) was routinely determined by the wall polymer level needed and was generally 5% to 50% of the final formulation. A skilled person in the art would be able to adjust the precursor amount, without undue experimentation, to prepare microcapsules having a desirable wall thickness and release profile.

A microscope image was taken for Microcapsule 1, showing that Microcapsule 1 was stable for at least two days when dried at room temperature (i.e., 25° C.) on a microscope slide. Further it had a higher mechanical stability than Comparative Microcapsule 2.

Microcapsule 1 thus prepared had a particle size ranging from 1 microns to 250 microns, and an Encapsulation efficiency (EE) of 73.0%.

Extractable Oil Analysis

EE is calculated as: $EE=[1-(Free\ oil/Total\ Oil)]\times 100\%$. The free oil is obtained from the free oil analysis. More specifically, 2 g of capsule sample and 6.7 g (approx. 10 mL) of hexanes are mixed in a vial, which is tumbled on a tube rotator (available from Scientific Equipment Products) for 10 minutes. The mixture is filtered into an autosampler vial and analyzed with a Agilent 7890A GC system with flame ionization detector (FID). The integrated area of each ingredient in the chromatogram is used to calculate the content level against a preestablished calibration curve.

Total oil analysis methods: In a 20 mL headspace vial, mix 0.2 g sample and 0.8 g water (or 1 g sample when sample is slurry) with 0.1 g of internal standard benzyl laurate. Add 10 ml of THF and cap the vial with a crimper. Sonicate the sample at 50° C. for 10 min. After the sample cools down in the refrigerator for about half an hour, open the vial with a decrimper and take the clear upper layer (or filter the upper layer if necessary) for GC analysis with a Agilent 7890A GC system with flame ionization detector (FID). The integrated area of each ingredient is used to calculate the content against a preestablished calibration curve.

Comparative Example 2

Another microcapsule of this invention, Comparative Microcapsule 2, was prepared following the same procedure as described in Example 1, except that 20 g TEOS was used instead of pretreated silica Poly-Si.

Extractable Oil analysis indicated an EE of 68.7%. The microscope image of Comparative Microcapsule 2 showed that Comparative Microcapsule 2 was unstable and collapsed within four hours when being dried on a microscope slide at room temperature.

Example 3

A third microcapsule of this invention, Microcapsule 3, was prepared following the procedure described below.

Step 1: Preparation of Fragrance Silica Microcapsule with Sorbitan Esters

A surfactant solution was prepared by mixing 1 g of Span 80 (Sorbitan monooleate, commercially available from Sigma-Aldrich) and 9 g of Tween 80 (Polyoxyethylene sorbitan monooleate, commercially available from Sigma-Aldrich) in 300 g of water under stirring for 2 hours. 100 g of this surfactant solution was added to an oil phase containing 10 g of pretreated silica Poly-Si, 25 g of a fragrance accord, and 5 g of Neobee oil. The resultant mixture was homogenized using an Ultra Turrax homogenizer at 9000 rpm for 3 minutes. The homogenizer was replaced by an overhead stirrer and the slurry was stirred at 400 rpm and the pH was adjusted to 8.5 with a diluted ammonia solution. The mixture was stirred at room temperature for 16 hours to obtain a capsule slurry containing a silica microcapsule.

Extractable oil analysis indicated an EE of 0.0%.

Step 2: Coating with Gum Arabic and Gelatin

An aqueous solution was prepared by mixing 200 g of a 2% Gelatin aqueous solution and 43 g of a 25% Gum Arabic aqueous solution in 200 g of water at 50° C. To this aqueous solution was added 50 g of the capsule slurry prepared in Step 1 above. The resultant mixture was stirred at 50° C. and the pH was adjusted to 3.5 with 1 N HCl aqueous solution. Curing under stirring at room temperature for 16 hours gave a microcapsule composition containing Microcapsule 3.

Extractable oil analysis indicated an EE of 83.3%. The microscope image of Microcapsule 3 showed that the microcapsule was stable when being dried on a microscope slide at room temperature.

Example 4

Another microcapsule of this invention, i.e., Microcapsule 4, was prepared following the procedure below.

A sol gel mixture was prepared by adding 30 g of pretreated silica Poly-Si and 40 g of lemon flavor oil (commercially available from International Flavors & Fragrances, South Brunswick, N.J.). To this sol-gel mixture was added 180 g of 10% purity gum ultra aqueous solution. The resultant mixture was homogenized with an Ultra Turrax homogenizer at 10000 rpm for 2 minutes to obtain a microcapsule slurry. Chitosan (3.6 g in 360 g of 1% aqueous solution) was added. The resulting microcapsule slurry was stirred at room temperature for 24 hours to obtain Microcapsule 4.

Extractable oil analysis indicated an EE of 84.5%. The microscope image of Microcapsule 4 showed that it was stable for at least 2 days after being dried on a microscope slide at room temperature.

Examples 5 and 6

Microcapsule 5 was prepared following the process described in Example 1 above using a model corn flavor at a load of 47% by weight of the microcapsule. The model corn flavor contained 90 wt % of Neobee oil and 10 wt % of the following ingredients each at a concentration of 0.005-2%: acetyl propionyl, acetyl methyl carbinol, maltol, methional, 2-acetyl-pyridine, dimeth sulf mx1450, 2,3,5-trimethyl pyrazine, vanillin, butyric acid, amyl vinyl carbinol, 2-octenal, delta-decalactone, delta-dodecalactone, and sacrazole. Microcapsule 5 was filtered from the microcapsule slurry, air dried, and collected as a powder.

Another microcapsule, i.e., Microcapsule 6, was also prepared at a hydrophilic flavor load of 47 wt %. Hydrophilic flavors include those having a C log P of 1 or less. Examples are acetyl propionyl, acetyl methyl carbinol, maltol, methional, 2-acetyl-pyridine, dimeth sulf mx1450, 2,3,5-trimethyl pyrazine. Microcapsule 6 was filtered from the microcapsule slurry, air dried, and collected as a powder.

Microcapsule 5 was mixed with Microcapsule 6 at a weight ratio of 3:1 to obtain Microcapsule 7.

Two crackers, i.e., Samples 1 and 2 were prepared using Microcapsules 5 and 7 respectively. Sample 1 was prepared using 0.165 wt % of Microcapsule 5. Sample 2 was prepared with 0.22 wt % of Microcapsule 7. Note that Sample 2 contained 0.165 wt % Microcapsule 5 and 0.055 wt % of Microcapsule 6. Each sample contained the following ingredients (all by weight of the sample): King Arthur AP Flour 63.3%, salt 0.95%, sugar 1.94%, butter 9.5%, microcapsules 5 or 7 (0.165% or 0.22%), and water q.s. to 100%.

A cracker dough was prepared by mixing and kneading the above ingredients. It was cut into individual crackers and baked at 400° F. for 8 minutes or until the edges of the crackers were slightly brown. Samples 1 and 2 thus prepared were cooled to room temperature and evaluated by a panel of 6 judges for the flavor strength and balance. The strength was score from 1 to 10, with 1 being a weak or no flavor, and 10 being a very strong flavor. The results indicated that Sample 2 had a cheese strength of 4.4. By contrast, Sample 1 had a cheese strength of 3.4. Further, the flavor of Sample 2 was more balanced than that of Sample 1.

Example 7

A spray dried capsule composition, Sample 3, was prepared following the process below.

A Cooler 2 Extra capsule slurry containing 8.3 wt % Cooler 2 Extra, 5.5 wt % wall material, and 86.2 wt % water was prepared following the process described in Example 1. Modified starch (1033 g) was added to 3726 g of the Cooler 2 Extra capsule slurry. The mixture was agitated vigorously until the solids were fully dispersed. The mixture was then spray dried to obtain product Sample 3.

The product had a flavor load of 20 wt %. Total oil analysis of the product found 20% Cooler 2 Extra (100% retention of flavor). Extractable oil analysis indicated an EE of 74%.

Analytical Evaluation of Flavor Delivery by Microcapsule

Chewing gum samples were prepared with lemon flavor oil, or microcapsule containing the same flavor oil, at a level that both gum samples contain 0.5% of lemon oil. The samples were processed with an artificial mouth and the water extracts were analyzed by GC. The flavor oil measured in the liquid extract was interpreted as the quantity of the flavor oil delivered. The results showed that microcapsule delivered 3.4% of the total oil loaded in gum, vs 2.6% from the gum made with neat oil, a 30.8% improvement.

Betty Crocker sugar cookie samples were prepared by mixing the wet dough with lemon flavor oil, or microcapsule containing the same flavor oil, at a level that the final baked cookies contain 1% of lemon oil. The cookie samples were analyzed with the total oil analysis protocol described previously. The flavor oil measured was interpreted as the quantity of the flavor oil delivered. The results showed that microcapsule delivered 4.1% of the total oil, vs 2.7% from the cookies made with neat oil, a 51.9% improvement.

Microcapsule Performance in Chewing Gums

Microcapsule 1 was prepared with Cooler 2 Extra (a cooling agent commercially available from IFF, Union Beach, N.J.) following the same procedure described previously. Chewing gum samples, i.e., Samples 3, 4, and 5, were prepared with Cooler 2 at a level of 1 wt %. Sample 3 contained neat Cooler 2 Extra. Sample 4 contained Cooler 2 Extra encapsulated in a gum-gelatin coacervate. Sample 5 contained Microcapsule 1. All three samples were evaluated by a panel of 6 judges for intensity scored on a scale of 1-10 with 1 being a weak or no flavor, and 10 being a very strong flavor. Unexpectedly, Sample 5 delivered a similar or stronger cooling sensation than Samples 3 and 4 at all points during the 15 minutes chewing evaluation. The table below showed the flavor strengths of the three samples at different time points.

TABLE 1

Flavor Strength in chewing gum evaluation

|  | Minute 1 | Minute 4 | Minute 7 | Minute 12 |
|---|---|---|---|---|
| Sample 3 | 3.125 | 2.25 | 2 | 1.625 |
| Sample 4 | 3.5 | 3 | 2.375 | 1.875 |
| Sample 5 | 3.5 | 3.375 | 3.125 | 2.25 |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of preparing a microcapsule suitable for delivering flavors, one skilled in the art can choose different dispersant, additional wall polymer precursors, and/or partially crosslinked silica, varying the concentrations of these wall-forming materials and/or catalysts to achieve a desirable organoleptic release profile in a consumer product. Further, the ratios among their wall-forming materials, dispersants, adjuvents, core modifiers, and active materials can also be determined by a skilled artisan without undue experimentation.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A microcapsule comprising: (i) a microcapsule core containing an active material, and (ii) a microcapsule wall formed of a first polymer and second polymer, wherein the first polymer is a sol-gel polymer, the second polymer is gum arabic, purity gum ultra, gelatin, chitosan, xanthan gum, plant gum, carboxymethyl cellulose, sodium carboxymethyl guar gum, or a combination thereof, and the weight ratio between the first and second polymer is 1:10 to 10:1, wherein the microcapsule wall is single-layered containing a polymeric network of polymerized silica interlocked with a coacervate of the second polymer wherein the sol-gel polymer is a silica polymer and the second polymer is a combination of gelatin and gum Arabic, and the weight ratio between gum Arabic and gelatin is 1:5 to 5:1.

2. The microcapsule of claim 1 furthering comprising a dispersant selected from the group consisting of quillaja saponin, N-lauroyl-L-arginine ethyl ester, sorbitan esters, lecithins, lyso-lecithins, polyethoxylated sorbitan esters, polyglyceryl esters, fatty acid esters, gum arabic, pectin, carrageenan, chitosan, chondroitin sulfate, cellulose gum, modified starch, whey protein, pea protein, egg white protein, silk protein, gelatin of fish, proteins of porcine or bovine origin, ester gum, fatty acids, and combinations thereof.

3. The microcapsule of claim 1, wherein the active material is a fragrance, pro-fragrance, flavor, malodor counteractive agent, anti-inflammatory agent, anesthetic, analgesic, anti-viral agent, anti-infectious agent, anti-acne agent, skin lightening agent, insect repellant, emollient, skin moisturizing agent, vitamin or derivative thereof, nanometer to micron size inorganic solid, polymeric or elastomeric particle, taste modulator, probiotic, cell, or combination thereof.

4. The microcapsule of claim 1, wherein the microcapsule has a particle size in diameter of 1 to 250 μm, and the weight ratio of between the microcapsule wall and the microcapsule core 1:50 to 2:1.

* * * * *